United States Patent [19]

Riehm

[11] Patent Number: 5,242,302

[45] Date of Patent: Sep. 7, 1993

[54] AMALGAM CONDENSER TOOL

[76] Inventor: Vincent J. Riehm, 5253 W. 111th ST., Bloomington, Minn. 55437-3301

[21] Appl. No.: 829,926

[22] Filed: Feb. 3, 1992

[51] Int. Cl.⁵ .............................................. A61C 3/08
[52] U.S. Cl. ..................................................... 433/164
[58] Field of Search ............... 433/164, 141, 150, 151, 433/83, 118

[56] References Cited

U.S. PATENT DOCUMENTS

| D. 26,678 | 2/1987 | Ivory. | |
|---|---|---|---|
| D. 275,992 | 10/1984 | Detsch. | |
| D. 297,565 | 9/1988 | Hamilton et al.. | |
| 532,721 | 1/1895 | Dennis | 433/164 |
| 536,327 | 3/1895 | Crymes. | |
| 712,576 | 11/1902 | McMath. | |
| 815,040 | 3/1906 | Rrtterford | 433/83 |
| 1,493,581 | 5/1924 | Watts. | |
| 1,676,715 | 7/1928 | Snyder | 433/164 |
| 2,696,048 | 12/1954 | Lindgren | 433/164 |
| 3,792,530 | 2/1974 | Smith. | |
| 4,306,863 | 12/1981 | Law et al. | 433/164 |
| 4,586,901 | 5/1986 | Tanaka et al. | 433/164 |
| 4,797,866 | 3/1931 | Ivory. | |

OTHER PUBLICATIONS

IDE Interstate Dental Supply Catalog, Spring/Summer 1992, pp. 79, 99, 106, 114 and 125.
Henry Schein Inc. Dental Catalog, Winter '91/Spring '92, pp. 166 and 168.
Declaration of Vincent J. Riehm, Apr. 21, 1992.

*Primary Examiner*—Cary E. O'Connor
*Attorney, Agent, or Firm*—Kinney & Lange

[57] ABSTRACT

A dental tool for compressing filling materials in a bore of a tooth. The dental tool includes an elongate member having a tip portion with a surface for contacting the filling materials. A portion of the contact surface of the tip segment is concave.

12 Claims, 4 Drawing Sheets

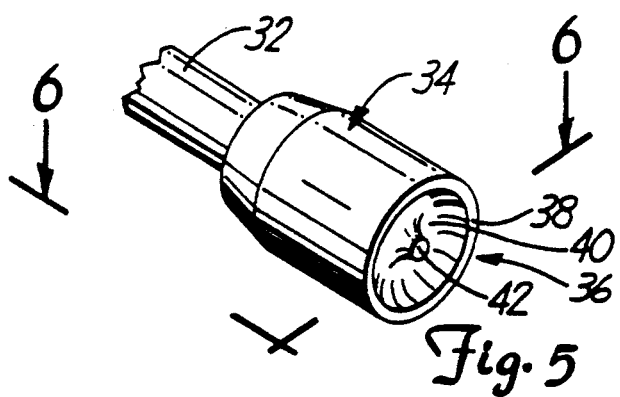
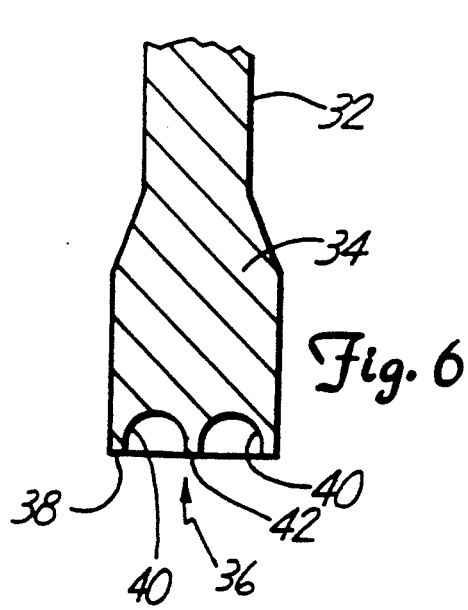
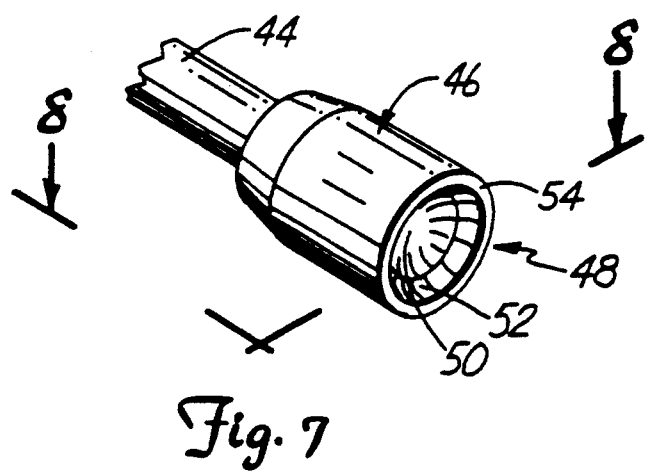
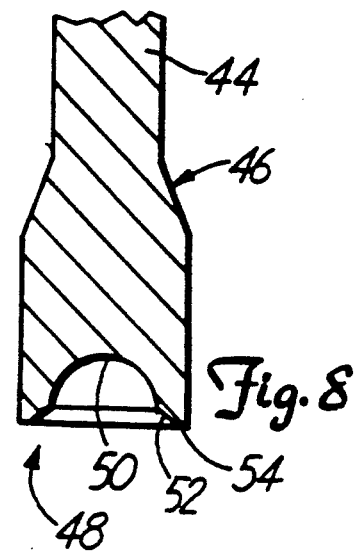
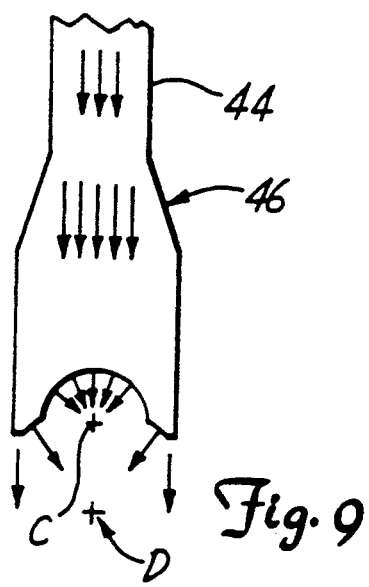

AMALGAM CONDENSER TOOL

BACKGROUND OF THE INVENTION

The present invention relates generally to dental tools for administering filling materials in a tooth. In particular, the present invention relates to a condenser tool for compressing filling materials into a bore of a tooth.

In the dental field, dentists and their assistants are required to fill cavities in decaying teeth. To do so, the dentist first creates a bore in the tooth thereby removing the area of decay. The bore is made larger in the bottom portions of the tooth than the upper portions of the tooth. Next, the bore is filled with a semi-liquid amalgam filling material or a similar metal mixture which later hardens into a solid. The amalgam filling becomes mechanically fixed within the bore because the bore is larger in the bottom portion than in the top so that upon a hardening of the amalgam, the amalgam is anchored within the bore.

Amalgam is a metal mixture typically including mercury and silver, which is prepared and maintained in a semi-liquid state similar to a paste. The amalgam sets into a solid mixture over time in a manner similar to a stone cement. An amalgam carrier tool is used to deliver the amalgam from an amalgam preparation area to mouth of the patient and into the bore in the tooth. The amalgam is then dispensed into the bore in the tooth and pushed down into the bore with a packing or condenser tool to insure that the amalgam has completely filled in the bore of the tooth.

Filling materials other than amalgam can be used to fill in a bore of a tooth. For example, composite filling materials sometimes are used that include either plastic materials or ceramic materials. These composite filling materials are placed within the bore of a tooth and condensed therein with an amalgam condenser tool in a manner similar to that described herein for amalgam filling material.

Conventional tools used for condensing amalgam into a bore have a tip segment that extends outwardly from a body of the tool and that has a surface for contacting the filling material. This contact surface is typically flat and smooth. Alternatively, the contact surface of the condenser tip is flat with a raised crosshatching formed on the contact surface. The dentist uses the contact surface of the condenser tip segment to compress the amalgam filling material into the bore.

Typically the amalgam is installed into the bore in several layers with the dentist using the condenser tool to compress the amalgam into the bore after each layer is installed. The dentist typically compresses the amalgam filling material down into the bore about five times for each layer of amalgam. This ensures that all portions of the amalgam layer have been compressed. A condenser tool with a smaller tip is used for reaching tight spots in the bottom of bore. Afterward, a condenser with a larger tip is used as more amalgam layers are added near the top. The dentist will typically add the layers of amalgam until the bore has been over packed with filling material The dentist then uses a carver tool to remove excess filling material from the top of the tooth. Last, the dentist uses a burnishing tool to shape and polish the top surface of the filling into a smooth contour with the tooth surface.

Several disadvantages plague conventional amalgam condenser tools. As previously discussed, some conventional condenser tools have tips segments with crosshatched contact surfaces for packing the amalgam. Condenser tools with the crosshatched contact surface suffer from a great disadvantage because that surface is susceptible to amalgam building up on the contact surface. The amalgam, once adhered to the crosshatched contact surface, remains thereon even after ultrasonic cleaning and steam autoclaving. Thus, to maintain a clean crosshatched contact surface, the dental practitioner must later clean off the tool with a pick or scraping device.

Moreover, this amalgam build up on the tip of the condenser tool is much more than an inconvenience. The amalgam build up makes it more difficult for the dentist to direct and compress the amalgam filling material in the desired direction. In particular, the amount of compressive force that actually acts on the amalgam decreases because the tip buildup causes the filling material to be pushed off to the side of the tip instead of remaining directly below the contact surface of the tip. To avoid these problems associated with having a condenser tool having a crosshatched tip surface, the dentist may grind off this crosshatching to create a smooth surface tip, or may even discard the tool altogether.

On the crosshatch style of condenser tip where amalgam may occasionally be trapped in the crosshatches even after being sterilized in a steam autoclave, it is theoretically possible that bacteria, viruses or spores may be trapped in between the adherent amalgam and the crosshatch tip. Since an autoclave is designed to sterilize clean, dry items, it may not sterilize a crosshatch style condenser tip that has amalgam trapped on its tip. Since this amalgam was used in a patient's mouth and may occasionally be mixed with saliva or blood, it could contribute to cross-contamination by surviving bacteria, viruses or spores to the next patient or a dental health care worker.

One advantageous feature of having a cross-hatched tip surface is that, after compressing the filling material with this tip surface, a crosshatch impression is formed in the top surface of the amalgam layer at the point at which the tip was pressed. This press point crosshatch impression in the amalgam layer permits the dentist to observe which areas of the amalgam layer have been compressed. This advantageously allows the dentist to ensure that all areas of each amalgam layer are fully compressed before packing the next layer of amalgam into the bore.

However, this advantage of using the cross-hatch tip sometimes vanishes upon regular use of the crosshatch tip condenser tool because of the previously described amalgam build up effect that occurs with regular use of the crosshatched tip tool. The amalgam build up prevents the crosshatch tip surface from forming the crosshatch impression in the amalgam layer surface. Moreover, because the amalgam build up makes the contact surface of the tip irregularly shaped, it becomes even more difficult to identify which areas of the amalgam layer have been compressed. Because of these problems associated with amalgam buildup on the crosshatch tip surface, a dentist often grinds off this crosshatching thereby forfeiting the advantage of locating press points in the amalgam layer by means of the crosshatch impression.

Problems also arise when the crosshatch tip surface is used to condense composite filling materials. When using a crosshatch condenser tip surface to pack composite filling materials, the top layer of filling material tends to adhere to the crosshatch surface. In particular, after pressing the condenser tip contact surface downward onto the filling layer and then withdrawing the contact surface back out of the top layer, the top layer of composite filling material adheres to the crosshatch surface and is pulled outwardly from the bore. Because the lower layers of composite filling material are bound to the top layer of composite material, when the top layer is pulled outwardly from the bore, the lower layers are also pulled out from the bore. As the crosshatch surface effectively tugs a major portion of the entire composite filling back out of the bore, the filling material partially separates from a wall of the bore creating voids in the interface between the bore wall and the filling material. The voids created by the tug back effect are undesirable and should be avoided. Indeed, it is for the precise reason of preventing the formation of voids that such care is taken in sufficiently compressing the filling materials into the bore. Thus, the use of conventional crosshatch tip surface is undesirable when compressing composite filling materials. It is believed that this tug back phenomenon occurs because the composite filling material more easily adhere to the acute angles formed between the raised portions of the crosshatch surface than a smooth contour surface.

Other significant disadvantages are present when using conventional condenser tools to compress filling materials (amalgam or otherwise) into the bore of a tooth. For example, as the dentist uses the condenser tip to apply compressive force to the amalgam, the flat surface of the tip causes the material to squeeze out from under the tip. This squeezing out of the material from under the tip results in attenuating the amount of compressive force applied by the dentist that actually gets transmitted to the amalgam layer. Moreover, recall that the amalgam filling, once hardened, is not adhesively attached within the bore but instead forms a mechanical connection within the bore of tooth. Thus, because the filling material must be mechanically fixed within the bore and because the material tends to squeeze out while being compressed, the dentist must perform many forceful downward pressing motions to ensure that sufficient compressive force has been applied to the amalgam in the bore.

Another, more significant problem associated with the use of conventional condenser tools complicates the application of sufficient compressive force to the amalgam filling. Over several years of administering fillings on a daily basis, the dentist may suffer pain and reduced mobility in the wrist of the hand used to compress the fillings. This pain and reduced mobility in the wrist hampers the dentist's ability to apply sufficient compressive force to the fillings. More importantly, this pain and reduced mobility in the wrist of the dentist is a chronic problem with long term deleterious effects usually associated with carpal tunnel syndrome.

Carpal tunnel syndrome includes the symptoms of debilitating pain and reduced mobility of the wrist caused by long term repetitive flexion bending motions of the wrist, or long term static use of the wrist in a bent flexion position. The carpal tunnel is a semicircular ring of bones in the wrist which defines a passageway for several tendons and nerves to pass from the forearm through the wrist into the hand. The pain and reduced mobility are caused by pressure exerted on the median nerve (extending through the carpal tunnel) by the tendons and bones which compress and rub against the nerve while the wrist is in the bent flexion position.

The particular motion of the dentist's wrist while compressing fillings and examining teeth make the dentist particularly susceptible to suffering from carpal tunnel syndrome. To compress the amalgam filling material into the bore of the tooth, the dentist typically grasps the condenser tool by holding the tip segment of the tool between the index finger, middle finger, and thumb of a hand with the body of the tool extending rearwardly towards and resting on the base of the index finger. Next, while so grasping the tool, the dentist positions the tip of the condenser tool onto the amalgam filling material within the bore of the tooth. The dentist then bends and maintains the wrist into a bent flexion position and then pushes downwardly with the arm to force the tip of the condenser tool into the filling material. Alternatively, the dentist will compress the filling by bending the wrist in flexion to generate the force to compress the amalgam filling material (without using the whole arm to push downwardly). Under either manner of pressing the tip onto the filling material, the dentist must perform a high force bent wrist flexion motion. Because each layer of a filling must be compressed about five times, it is apparent that this high force bent flexion motion of the wrist will be performed many times for each filling and tooth. Moreover, accounting for the number of patients seen daily, it is obvious that this pressing motion is repeated very many times daily. This is the kind of activity that results in carpal tunnel syndrome.

In addition to performing this motion while packing amalgam fillings, the dentist also frequently performs this high force bent wrist flexion motion during a routine dental examination. A dentist can determine that a tooth is decaying if a sharp pointed object is pressed into the tooth surface and the tooth surface tends to retain the tip upon trying to withdraw the sharp tip from the tooth. To perform this test, the dentist presses a sharp tipped elongate tool downwardly (with substantial force) into the tooth surface in the same bent wrist flexion motion previously described for compressing fillings. The dentist must perform this motion several times for each tooth. Thus, during the course of a typical day, the dentist is constantly required to make this high force, bent wrist flexion motion while examining teeth. This stress on the wrist from routine dental examinations compounds the likelihood of the dentist suffering from the long term pain and reduced mobility associated with carpal tunnel syndrome.

Carpal tunnel syndrome is a serious common problem afflicting individuals in work environments in which this high force, bent wrist flexion motion repeatedly occurs. For example, in addition to dentists, workers having the following occupations are susceptible to this syndrome because of the repetitive or continuous stress on the wrists in the bent flexion position: typists, heavy equipment operators, jackhammer operators, cold steel chisel workers, truck drivers, and assembly plant workers. This syndrome results in missed work, workers compensation claims, and lower productivity. Moreover, the pain and reduced mobility hamper the individual's ability to engage in leisure time and household activities, and may ultimately lead to surgery as a treatment option. Thus, this problem found in dentistry is not an isolated instance of occupation specific injury but part of a larger significant problem that has a deleterious effect on workers in many industries.

Several disadvantages are apparent in the conventional condenser tools. First, the conventional condenser tools have flat tip surfaces which tend to cause the filling material to be squeezed out from under the tip surface. This causes a loss of the force applied by the dentist thereby requiring the dentist to exert more effort to apply a sufficient compressive force to the filling. This, in turn, exacerbates the previously discussed stress on the wrist resulting from the dentist's frequent high force, bent wrist flexion pressing motions that cause carpal tunnel syndrome. Second, because of the amalgam build up effect on the crosshatch type tip surface, the tip surfaces do not leave the advantageous press point impressions on the filling surface. Moreover, the amalgam build up problem hinders the dentist's ability to direct the filling material in the desired direction with the minimum amount of force applied. This too compounds the previously described factors which make the dentist susceptible to suffering from carpal tunnel syndrome.

In addition, when the crosshatch tip surface is used to compress composite filling materials, a tug back effect occurs that creates voids between the wall of the bore and the installed layers of filling material. This requires the dentist to make even more bent wrist flexion motions to ensure proper fixation between the bore wall and filling material. Moreover, the disadvantages of using a crosshatched tip surface are further exacerbated when that tip is used with composite filling materials.

SUMMARY OF THE INVENTION

Unlike the previous dental tools used for compressing filling materials into a bore of a tooth, the dental tool of the present invention alleviates the symptoms of carpal tunnel syndrome resulting from the dentists' repetitive, high force, bent wrist pressing motions involved in compressing fillings.

The dental tool of the present invention comprises an elongate member having a tip segment with a surface for contacting the filling materials, in which a portion of the contact surface is concave. In one preferred embodiment of the present invention, a flat surface rim forms the edge of the concave portion of the contact surface. Alternatively, the surface of the rim is formed to have an undulating (or wavy) shape surface. The depth and width of the concave portion of the condenser tip may be increased or decreased to achieve the desired compressive effect.

In another embodiment, in addition to the flat surface (or undulating surface) rim, a stem extends outwardly from the center of the concave portion of the contact surface. The stem is positioned substantially parallel to the longitudinal axis of the tip portion.

The amalgam condenser tool of the present invention results in a better application of compressive force onto the amalgam filling material. The concave shaped tip surface focuses the applied compressive forces inwardly toward the focal point of the contact surface permitting a more efficient transmission of the compressive force from the dentist's wrist to the amalgam (or other filling material). In addition, the flat surface rim of the concave condenser tip surface prevents the filling materials from squeezing out from under the concave contact surface of the tip. This effect can be accentuated with the undulating surface rim which facilitates anchoring the contact surface into the top amalgam layer during the compressive action. In combination, these effects of the concave tip surface of the present invention result in more compressive force being transmitted from the dentist's wrist onto the amalgam filling. In turn, this effect reduces the amount of force that must be exerted through the wrist of the dentist when compressing fillings. Over a long period of time of using the concave condenser tip surface of the present invention, this reduced force on the wrist alleviates the pain and reduced mobility of the wrist associated with carpal tunnel syndrome. This permits the dentist to work relatively pain-free and be free to pursue leisure and household activities without being hindered by the symptoms of carpal tunnel syndrome.

In addition, upon compressing amalgam with the inventive concave condenser tip surface, a dome-shaped press point impression is created in the amalgam layer surface. The dome-shaped press points allow the dentist to identify which areas of the filling material have been compressed. The concave tip of the present invention also avoids an amalgam build up effect because the concave surface is smooth and therefore does not provide a surface against which the amalgam may easily adhere. This leaves the tool cleaner for reuse, which is advantageous in avoiding the possibility of cross-contamination of patients. Moreover, even if some amalgam build up does occur, the concave condenser tip still focuses the compressive forces into the amalgam filling in a more concentrated fashion than the conventional tips and still leaves the distinctive dome-shaped press point impression in the amalgam filling.

BRIEF DESCRIPTION OF THE DRAWINGS

FIG. 5 is a perspective view of an alternative embodiment of the present invention including a flat surface stem forming a portion of the contact surface.

FIG. 6 is a sectional view taken along line 6—6 in FIG. 5.

FIG. 7 is a perspective view of an alternative embodiment of the present invention including two superimposed cavity contact surfaces.

FIG. 8 is a sectional view along lines 8—8 of FIG. 7.

FIG. 9 is a schematic representation of the compressive forces applied by the contact surfaces of the tool of FIG. 7.

Figure 12:
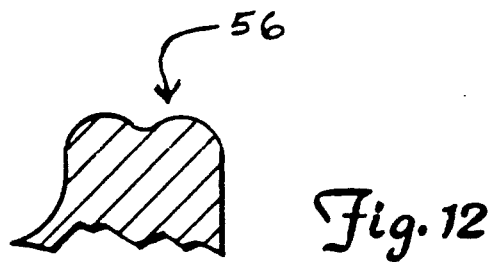
FIG. 12 is a sectional view along lines 12—12 of FIG. 10.

While the above-identified drawing figures set forth several preferred embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention. For instance, the sizes and shapes of the illustrated preferred embodiments are merely exemplary and are not the only sizes and shapes which embody the present invention. Also, the figures have not been drawn to scale as it has been necessary to enlarge certain portions for clarity. For instance, the radius of curvature for the concave surface portions depicted in the drawing figures are exaggerated relative to the dimensions of other portions of the tool. Likewise, the width of the rim in FIG. 12 is exaggerated relative to the dimensions of the other portion of the contact surface to enhance visualization of the undulating shape surface rim.

DETAILED DESCRIPTION OF THE PREFERRED EMBODIMENTS

Figure 1:
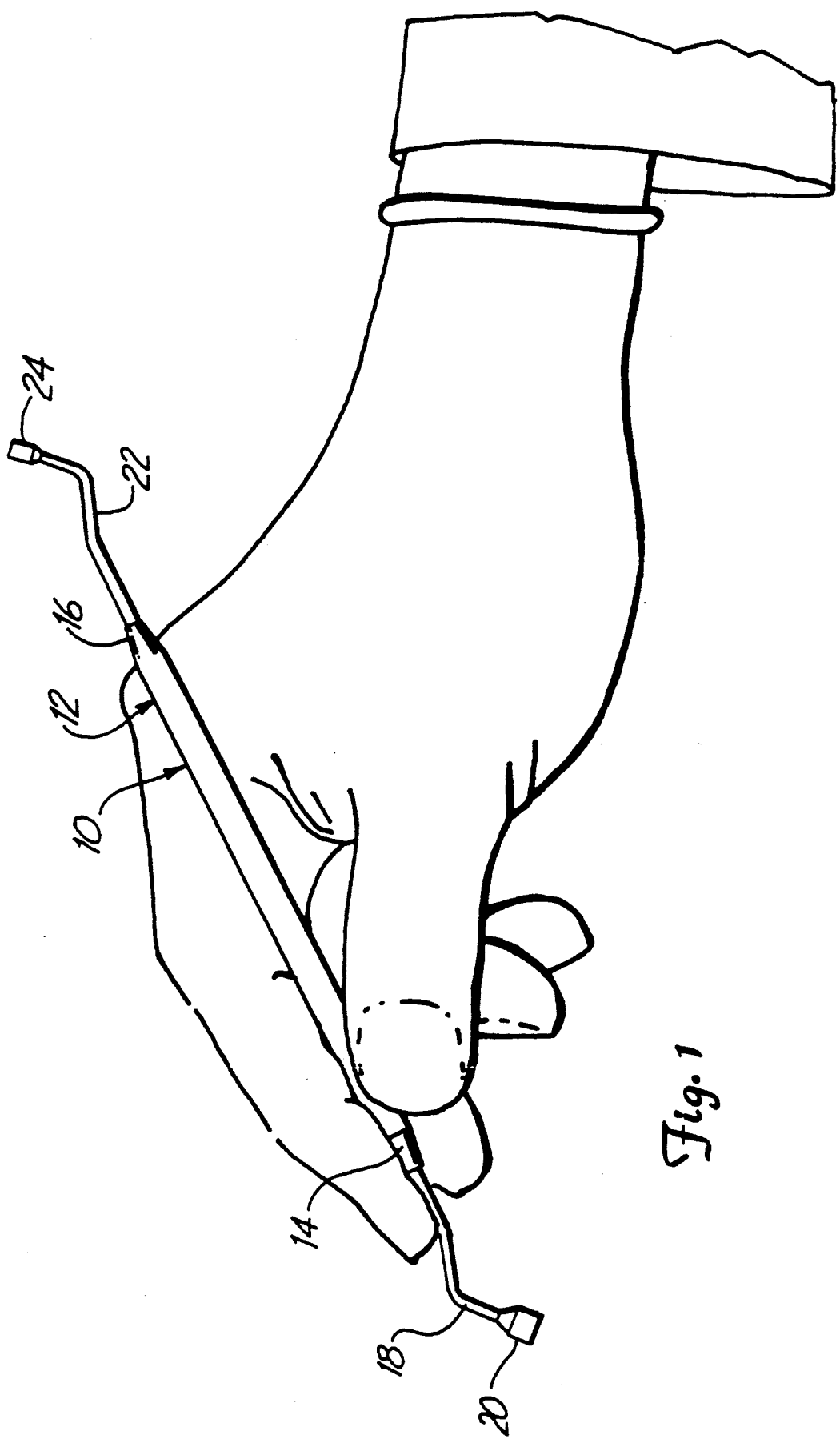
FIG. 1 is a side view in elevation of a dental tool of the present invention as typically held within a hand of a dentist.

The amalgam condenser tool of the present invention is illustrated generally at 10 in FIG. 1 as held within a hand of a dental practitioner. The condenser tool 10 has an elongate body 12 with a first end 14 and a second end 16. A first tip segment 18 extends outwardly from the first end 14 and has a tip portion 20. A second tip segment 22 extends outwardly from the second end 16 and has a tip portion 24. The condenser tool 10 is made of a stainless steel material or a nickel-chromium plated material. Alternatively, the condenser tool tip portions 20 and 24 can be made of other materials that are more compatible with, i.e., avoid adhering to, the previously discussed composite materials.

Figure 2:
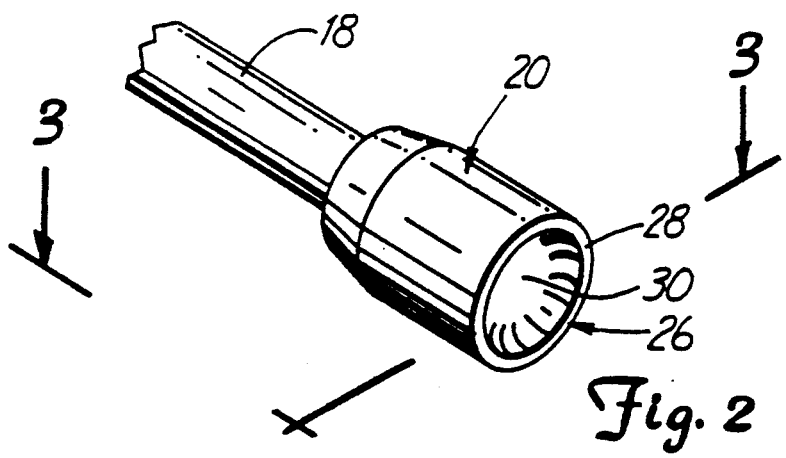
FIG. 2 is an enlarged perspective view of the contact surface of the condenser tip of the present invention.
Figure 3:
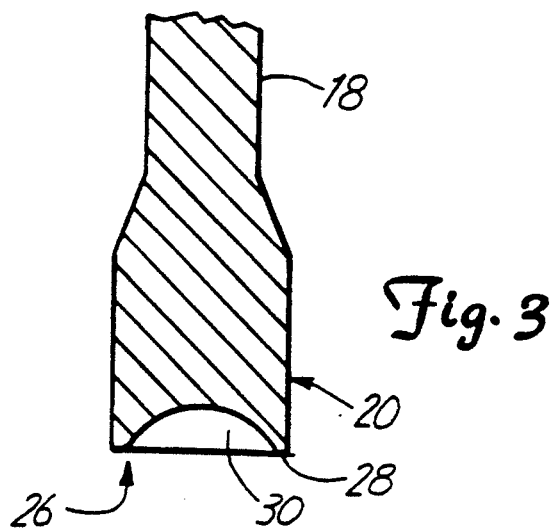
FIG. 3 is a sectional view of the contact surface of the condenser tip taken along line 3—3 of FIG. 2.

As seen in FIGS. 2 and 3, in a preferred embodiment of the present invention, the tip portion 20 of the first tip segment 18 includes a surface 26 for contacting amalgam filling material within a bore of a tooth. The contact surface 26 has a concave surface portion 30 formed in an end of the tip portion 20 and a flat surface rim portion 28 which defines the periphery of the concave surface portion 30.

The condenser tool of the present invention is used to compress filling materials into the bore of a tooth in a manner similar to that previously described for conventional condenser tools. First, the dentist creates a bore in the tooth thereby removing the area of decay from the tooth. Next, an amalgam carrier (another hand-held dental tool) is used to install a layer of semi-liquid amalgam paste into the bottom portion of the bore. The dentist then uses the condenser tool 10 of the present invention to compress the layer of amalgam into the bottom of the bore. To do so, the dentist first grasps the condenser tool 10 by holding the tip segment 18 (and first end 14) between the index finger, middle finger, and thumb of the hand such that the body 12 of the tool extends rearwardly toward and rests on the base of the index finger. While so grasping the tool 10, the dentist positions the contact surface 26 of the tip portion 20 of tool 10 onto the amalgam filling material in the bore. The dentist then bends the wrist in flexion to force the concave surface portion 30 downwardly onto the amalgam thereby compressing the semi-liquid amalgam within the bore. The dentist then removes the contact surface 26 of the condenser tip 20 from the surface of the amalgam layer.

After such an amalgam compression, the concave surface portion 30 of condenser tip 20 leaves a dome-shaped impression or press point in the semi-hardened amalgam layer indicating the location of the area of the amalgam layer which has been compressed. The dentist, at this point of the procedure, may remove the condenser tip 20 from within the bore of the tooth to observe the press point. However, typically, the dentist repositions the contact surface portion 26 of the condenser tip 20 onto an uncompressed portion of the amalgam layer without observing the location of the first press point. The dentist then once again bends the wrist in flexion forcing the concave surface portion 30 downwardly onto the amalgam layer thereby compressing the amalgam within the bore and also forming another press point. These steps of repositioning and compressing are repeated until all portions of the amalgam layer are believed to have been compressed.

Next, the dentist removes the condenser tip 20 from within the bore to determine whether all portions of the amalgam layer have been compressed by observing the location of the press points in the amalgam layer. If it appears that all portions of the amalgam layer have been compressed, then the dentist uses the amalgam carrier to install another layer of amalgam into the bore on top of the first amalgam layer. The dentist once again positions the contact surface 26 of condenser tip 20 onto the amalgam layer and bends the wrist in flexion to force the concave surface portion 30 into the amalgam layer thereby compressing the amalgam. Again, the steps of repositioning and compressing are repeated until all portions of the amalgam layer have been compressed. In a similar fashion, additional layers of amalgam are added until the bore is over packed with amalgam filling material. The dentist then uses a carver tool to remove excess amalgam from the top surface of the tooth and a burnishing tool to shape and polish the top surface of the filling.

Figure 4:
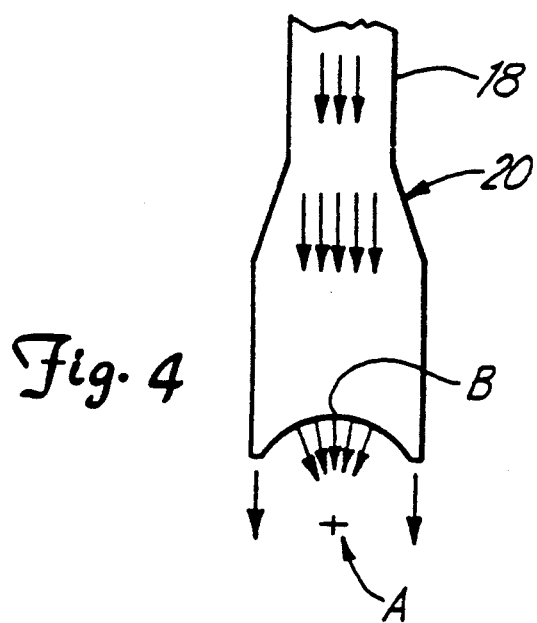
FIG. 4 is a side view in elevation schematically illustrating the manner in which a force is transmitted through the contact surface of the condenser tip of the present invention.

Compressing the amalgam filling material with the unique concave surface portion 30 of condenser tip 20 has significant advantages. First, the concave contact surface 30 accentuates the compressive forces applied by the dentist. The concave surface 30, as schematically illustrated in FIG. 4, focuses the energy transmitted through the condenser tip 20 into and through the amalgam (not shown) at point A. The flat surface rim 28 of the condenser tip 20 acts as a barrier to prevent amalgam from squeezing out from under the contact surface 26 of the condenser tip 20. This retains the focusing effect of the compressive forces caused by concave surface 30. In combination, the concave surface portion 30 and flat surface rim 28 act to transmit more compressive force from the condenser tip 20 into the amalgam (disposed directly under the contact surface 26) than the compressive force transmitted by conventional condenser tip surfaces. A distinct advantage is provided over conventional flat tip condenser tools in which the flat tip surfaces did not provide a barrier to prevent the amalgam from squeezing out from under the condenser tip and there was no mechanism for focusing the compressive forces to a focal point in the amalgam.

Moreover, the concave surface portion 30 of condenser tip 20 tends to stay cleaner after use than the conventional flat tip tools with crosshatched tip surfaces which were subject to amalgam build up. Because the concave surface portion 30 is smooth, the contact surface 26 can be used with composite filling materials while diminishing the tug back phenomenon that occurs when using the crosshatch tip surface.

Point A shown in the schematic illustration of force compression of FIG. 4 is the focal point of the concave surface 30. The distance between the focal point A and a center (point B) of the concave surface portion 30 is the focal length. The focal length is a function of the radius of the concavity of the concave surface portion 30 and can be made longer or shorter by respectively increasing or decreasing the radius of the concave surface 30. Thus, to have the majority of the compressive forces transmitted by concave surface portion 30 converge on the amalgam filling closer to the surface of the amalgam layer, the concave surface should be made with a radius of curvature smaller than that shown in FIG. 4. Alternatively, to have the majority of the compressive forces converge on the amalgam filling below the amalgam layer surface, the concave surface portion 30 should be made with a radius similar to that shown in FIG. 4. Thus, depending upon the desired compressive effect, the radius of the concave surface portion 30 may be chosen to appropriately enhance the transmission of compressive energy from condenser tip 20 into the amalgam.

The increased transmission of energy from the dentist's wrist to the amalgam filling has very significant ergonomic effects. First, using the condenser tip 20 of the present invention, the dentist is able to sufficiently compress the amalgam filling while exerting less effort in bending the wrist in flexion. Over a long period of time, such as thousands of amalgam compression wrist motions, this reduced effort required by the wrist results in diminished symptoms of carpal tunnel syndrome. Specifically, a dentist using the condenser tool 10 of the present invention having tip 20 with the concave surface portion 30 will realize less pain and increased mobility in the wrist. This results from the increased efficiency in transmitting compressive forces from the wrist into the amalgam by virtue of the combination of the concave surface portion 30 and flat surface rim 28 of the condenser tip 20 of the present invention. The reduction in pain and increased mobility in the wrist allows the dentist to more actively pursue leisure and household activities without being limited by the chronic pain associated with carpal tunnel syndrome. For instance, the dentist can engage in leisure activities which place weight bearing stress on the wrist and require full motion of the wrist. These voluntary stresses on the wrist are frequently not possible when suffering from carpal tunnel syndrome resulting from using a conventional condenser tool to compress amalgam fillings.

In addition to the particular shape of the concave surface 30 of condenser tip 20 illustrated in FIGS. 2 and 3, the concave surface portion 30 can have many different shapes as long as each includes some portion of concavity. For example, the concave surface 30 can have a depth shallower than or deeper than that shown in FIGS. 2 and 3. Similarly, the concave surface portion 30 could have a width (relative to the full width of the tip portion 20) greater than or narrower than that shown in FIGS. 2 and 3 provided that some flat surface rim 28 is retained.

The second tip portion 24 on the second end 16 of condenser tool 10 may include a tip for carving or burnishing amalgam filling material. Alternatively, the tip portion 24 of second tip segment 22 can be another concave surface portion like concave surface portion 30 of tip portion 20. In this instance, the second tip segment 22 can include a concave surface tip portion 24 having a different width or depth than, or the same width and depth as the concave surface portion 30 of the first tip segment 18. Alternatively, the second tip segment can include a concave surface tip portion 24 having a configuration like that described for embodiments other than tip portion 20.

In another embodiment, as seen in FIGS. 5 and 6, a tip segment 32 of the present invention includes a tip portion 34. The tip portion 34 has a contact surface portion 36 with a concave surface portion 40. The edge of the concave surface portion 40 is defined by a flat surface rim 38. A stem 42 extends outwardly from the concave surface 40 along a line substantially parallel to the longitudinal axis of tip portion 34. This stem, as seen in FIG. 5, forms a concave surface portion 40 which has annular-shaped concave surface.

This concave condenser tip 36 is used to compress amalgam fillings in the manner similar to that described for the concave condenser tip 20 of the first preferred embodiment. This arrangement of having the stem 42 extend from a center of the concave surface portion 36 allows for better and longer wear of the rim 38. Moreover, having the stem 42 in the center of the concave surface portion 36 creates a distinctive donut-shaped press point impression in the amalgam filling when the concave surface portion 36 is used to compress the amalgam.

In another embodiment, as seen in FIGS. 7 and 8, the condenser tool 10 of the present invention includes a tip segment 44 with a tip portion 46. The tip portion 46 has a contact surface 48 including a first concave surface portion 50 and a second concave surface portion 52. A flat surface rim portion 54 defines the edge of the concave surface portion 52.

The concave condenser tip 46 is used to compress amalgam fillings in the manner similar to that described for the concave condenser tip 20 of the first preferred embodiment. However, the first concave surface portion 50 has a smaller radius of curvature than the second concave surface portion 52. Similarly, the relationship of these two concave surface portions 50 and 52 can be understood as being two curves, each having a different radius of curvature, that are superimposed on each other such that the second concave portion 52 forms an annular ring extending about a circumference of the first concave portion 50. This results in the first concave surface portion 50, as seen in the perspective view of FIG. 7, being disposed concentric with and interior of the second concave surface portion 52.

As schematically illustrated in FIG. 9, this results in the condenser tip 46 creating two different focal points, C and D, at which the majority of compressive forces converge on the amalgam filling. Focal point C is the focal point of the first concave surface portion 50 and focal point D is the focal point of the second concave surface portion 52. Having a concave contact surface 48 with two different concave portions, each with a different focal point, permits the dentist to more evenly distribute (throughout the amalgam) the accentuated compressive effect created by the concave surface portions 50 and 52 and the flat surface rim 54. In this configuration, more of the compressive forces are transmitted by the contact surface converge on focal point C than on focal point D such that more compressive forces are applied closer to the amalgam layer surface than below the surface. This force distribution created by first concave portion 50 and second concave portion 52 is advantageous employed if applied to first few layers of amalgam filling at the bottom of the bore because the filling will be shallow then and compressive forces applied near the surface would be used maximally. Conversely, compressive forces converging beyond the bottom of the bore would be wasted.

Alternatively, for a slightly different distribution of compressive forces on the amalgam, the first concave surface portion 50 can be made with a slightly larger radius than that schematically illustrated in FIG. 9. As compared to the last example, this configuration would result in more compressive forces converging deeper below the surface of the amalgam filling. This force distribution would be advantageous when condensing amalgam during the last few layers when it is desired to periodically ensure the uniform compression of the amalgam throughout the filling. Likewise, if desired, concave surface portion 52 also be made with a larger radius to enhance the effect created by using the slightly larger radius first concave surface portion 50.

A dentist can employ both examples of this last embodiment on the same condenser tool. First, the dentist can form the condenser tool 10 with the tip segment 44 and the tip portion 46 as described. The dentist can then form tip portion 24 similar to tip portion 46 except for the concave surface portions of tip portion 24 having either larger or smaller radii of curvature than the concave surface portions 50 and 52 of tip portion 46.

Figure 10:
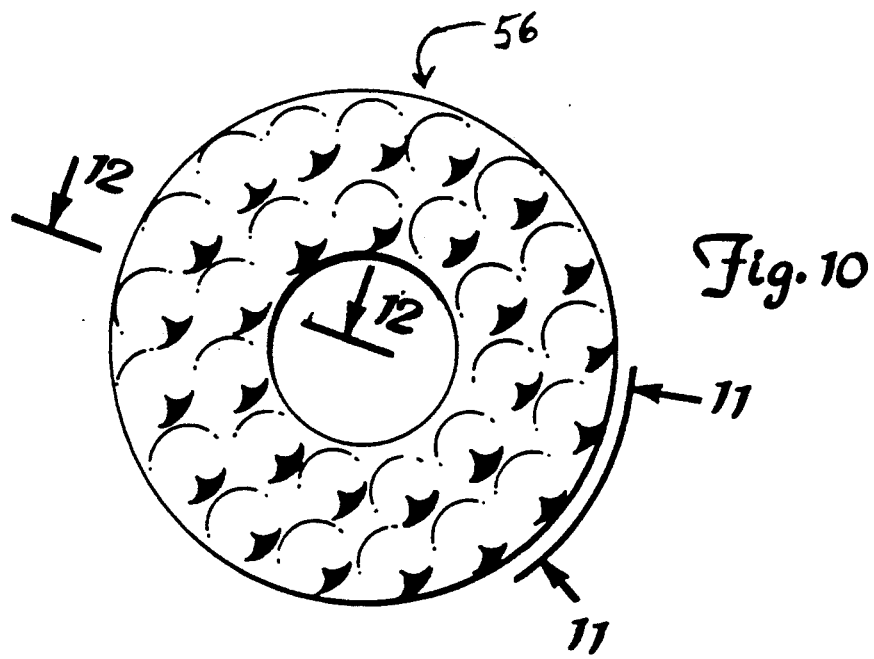
FIG. 10 is a end view of a variation of the embodiment shown in FIGS. 2-4 in which the rim of the concave surface portion has an undulatory shape.
Figure 11:
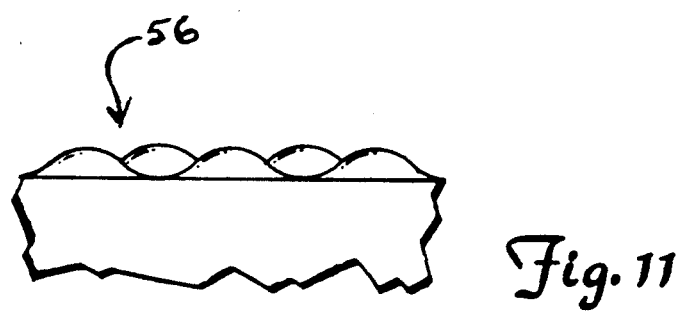
FIG. 11 is a sectional view along lines 11—11 of FIG. 10.

In the previously discussed embodiments, a flat surface rim formed the edge of the concave surface portion of the condenser tip. In a variation of those embodiments, as seen in FIGS. 10-12, a rim 56 of the contact surface (26, 36, or 48) has a undulating (or wavy) shape surface with a smooth contour. This undulating surface rim facilitates the seating of the rim into the amalgam layer to prevent slippage of the rim in the amalgam that occurs with a flat surface tip as the compressive forces are applied. This undulating surface ensures that the rim will act as a barrier preventing the amalgam from squeezing out and facilitates application of compressive forces at the desired site. In addition, the smooth contour of undulating surface rim 56 (see FIGS. 11 and 12) is believed to diminish the tendency of a composite filling material to adhere to a non-smooth contact surface. This smooth surface is in contrast to the acute angles between the raised portions of the conventional crosshatching tip surfaces, which are believed to cause the previously discussed tug back phenomenon.

The condenser tool of the present invention has many advantages over conventional condenser tools. The most important advantage is the increased mechanical efficiency in compressing the amalgam filling material that results from the concave condenser tip surface. This increased efficiency results in better compressed amalgam fillings and reduced strain on the wrist of the dentist in applying compressive force to the amalgam fillings. Using a concave surface tip condenser tool over a long period of time can alleviate symptoms of carpal tunnel syndrome that are the result of compressing amalgam fillings with conventional flat tip condenser tools. Moreover, the concave surface tip of the present invention forms distinctively shaped press point impressions (e.g., dome or donut-shaped) in the compressed amalgam allowing the dentist to determine which portions of the amalgam have been compressed. In addition, the concave surface portion condenser tip of the present invention tends to remain cleaner, i.e., having less amalgam build up, than the conventional condenser tools having crosshatched type flat tip surfaces. This reduces the labor and expense involved in maintaining dental equipment as well as conserving natural resources (fewer damaged tools are discarded) thereby delivering an overall reduction in the cost of dental services while increasing the quality.

Although the present invention has been described with reference to preferred embodiments, workers skilled in the art will recognize that changes may be made in form and detail without departing from the spirit and scope of the invention.

What is claimed is:

1. A dental tool for compressing filling materials in a bore of a tooth comprising:
   an elongate member having a tip portion with a surface for contacting the filling materials, a portion of the contact surface having an inner concave portion and an outer rim portion and being adapted to fit entirely within the bore of the tooth,
   the concave portion further comprising a first portion and a second portion, the first portion being disposed concentrically interior of the second portion and having a radius of curvature smaller than the second portion, the second portion defining an edge of the first portion and forming at least a portion of the outer rim portion.

2. A dental tool for compressing filling materials in a bore of a tooth comprising:
   an elongate member having a tip portion with a surface for contacting the filling materials, the contact surface having an inner concave portion and an outer rim portion and being adapted to fit entirely within the bore of the tooth,
   the concave portion further comprising a first portion and a second portion, the second portion forming an annular ring defining an edge of the first portion and forming at least a portion of the outer rim portion, the first portion having a smaller radius of curvature than the second portion.

3. A dental tool for compressing filling materials in a bore of a tooth comprising:
   an elongate member having a tip portion with a surface for contacting the filling materials, the contact surface having a concave portion and a flat surface rim forming an edge of the concave portion.

4. The dental tool of claim 3 wherein the contact surface further comprises:
   the concave portion having a first portion and a second portion, the first portion being disposed concentrically interior of the second portion, the first portion having a radius of curvature smaller than the second portion.

5. The dental tool of claim 3 wherein the contact surface further comprises:
   the concave portion having a first portion and a second portion, the second portion forming an annular ring extending about the circumference of the first portion, the first portion having a smaller radius of curvature than the second portion.

6. The dental tool of claim 3 and further comprising:
   a stem extending outwardly from the center of the concave portion of the contact surface and being substantially parallel to the longitudinal axis of the tip portion.

7. The dental tool of claim 6 wherein the concave portion is annularly shaped.

8. A dental tool for compressing filling materials in a bore of a tooth comprising:
   an elongate member having a tip portion with a surface for contacting the filling materials, the contact surface having a concave portion and an undulating shaped surface rim forming an edge of the concave portion.

9. The dental tool of claim 8 and further comprising:

a stem extending outwardly from the center of the concave portion of the contact surface and being substantially parallel to the longitudinal axis of the tip portion.

10. The dental tool of claim 8 wherein the contact surface further comprises:

the concave portion having a first portion and a second portion, the first portion being disposed concentrically interior of the second portion, the first portion having a radius of curvature smaller than the second portion.

11. The dental tool of claim 8 wherein the contact surface further comprises:

the concave portion having a first portion and a second portion, the second portion forming an annular ring extending about the circumference of the first portion, the first portion having a smaller radius of curvature than the second portion.

12. A dental tool for compressing filling materials in a bore of a tooth comprising:

an elongate member having a tip portion with an end surface for contacting the filling materials, the contact surface being adapted to fit entirely within the bore of the tooth and having a concave portion with a stem extending outwardly from the center of the concave portion and being substantially parallel to the longitudinal axis of the tip portion.

* * * * *